(12) United States Patent
Andersen et al.

(10) Patent No.: US 11,980,742 B2
(45) Date of Patent: May 14, 2024

(54) DRUG DELIVERY DEVICE WITH A HYDRAULIC TRIGGER MECHANISM

(71) Applicant: Novo Nordisk A/S, Bagsvaerd (DK)

(72) Inventors: Carsten Schau Andersen, Seattle, WA (US); Simon Roervig, Copenhagen OE (DK); Steffen Hansen, Hilleroed (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 15/533,567

(22) PCT Filed: Dec. 22, 2015

(86) PCT No.: PCT/EP2015/080961
§ 371 (c)(1),
(2) Date: Jun. 6, 2017

(87) PCT Pub. No.: WO2016/107789
PCT Pub. Date: Jul. 7, 2016

(65) Prior Publication Data
US 2017/0348486 A1    Dec. 7, 2017

(30) Foreign Application Priority Data

Dec. 29, 2014  (EP) .................................... 14200378
Jan. 7, 2015  (EP) .................................... 15150309

(51) Int. Cl.
*A61M 5/20*      (2006.01)
*A61M 5/24*      (2006.01)
(Continued)

(52) U.S. Cl.
CPC ........ *A61M 5/2033* (2013.01); *A61M 5/2459* (2013.01); *A61M 5/31536* (2013.01);
(Continued)

(58) Field of Classification Search
CPC .............. A61M 5/2033; A61M 5/2422; A61M 5/2425; A61M 5/2429; A61M 5/281;
(Continued)

(56) References Cited

U.S. PATENT DOCUMENTS 3,403,680 A * 10/1968 Cyril ................... A61M 5/2033
  604/138
3,797,489 A *  3/1974 Sarnoff ............... A61M 5/2033
  604/136
(Continued)

FOREIGN PATENT DOCUMENTS

DE      102011119058 B3   11/2012
EP          1379299 A1     1/2004
(Continued)

*Primary Examiner* — Kami A Bosworth
(74) *Attorney, Agent, or Firm* — Wesley Nicolas

(57) ABSTRACT

A device for administering a fluid medicament by injection comprises a dosing portion (1) with a collapsible reservoir (10). The reservoir (10) has a maximum volume in an extended state and a minimum volume in a collapsed state. Prior to injection, the reservoir (10) is in the extended state and contains a liquid to be administered, and the reservoir (10) is biased towards the collapsed state. The device further comprises a needle (2), wherein a lumen (20) of the needle (2) is in fluid communication with the reservoir (10). The device further comprises a shield portion (3) with a plug (30). Prior to injection, the shield portion (3) is in a deployed position where the plug (30) blocks the lumen (20) of the needle (2). The shield portion (3) is adapted to move in response to an actuation force from the deployed position to a retracted position where the lumen (20) of the needle (2) is open, thereby causing the reservoir (10) to shift to the collapsed state to expel the liquid through the needle.

17 Claims, 2 Drawing Sheets

(51) Int. Cl.
*A61M 5/315* (2006.01)
*A61M 5/32* (2006.01)
*A61M 5/31* (2006.01)
*A61M 5/46* (2006.01)

(52) U.S. Cl.
CPC ...... *A61M 5/31591* (2013.01); *A61M 5/3202* (2013.01); *A61M 5/3204* (2013.01); *A61M 5/3232* (2013.01); *A61M 5/3243* (2013.01); *A61M 2005/2013* (2013.01); *A61M 2005/206* (2013.01); *A61M 2005/3109* (2013.01); *A61M 2005/3154* (2013.01); *A61M 2005/3254* (2013.01); *A61M 2005/3267* (2013.01); *A61M 5/46* (2013.01)

(58) Field of Classification Search
CPC .. A61M 5/282; A61M 5/283; A61M 5/31591; A61M 5/3243; A61M 2005/2013; A61M 2005/2026; A61M 2005/206; A61M 2005/208; A61M 2005/3267; A61M 5/285; A61M 5/288; A61M 2005/3107; A61M 2005/3109; A61M 2005/311; A61M 2005/312
See application file for complete search history.

(56) References Cited

U.S. PATENT DOCUMENTS

| | | | | |
|---|---|---|---|---|
| 3,892,237 | A * | 7/1975 | Steiner | A61M 5/2053 604/157 |
| 3,911,916 | A | 10/1975 | Stevens | |
| 3,958,570 | A * | 5/1976 | Vogelman | A61M 5/24 604/206 |
| 4,227,528 | A | 10/1980 | Wardlaw | |
| 4,237,876 | A | 12/1980 | Rumph et al. | |
| 4,258,713 | A | 3/1981 | Wardlaw | |
| 4,553,962 | A | 11/1985 | Brunet | |
| 5,201,708 | A * | 4/1993 | Martin | A61M 5/3271 604/110 |
| 5,298,024 | A | 3/1994 | Richmond | |
| 5,540,664 | A * | 7/1996 | Wyrick | A61M 5/002 604/135 |
| 5,779,677 | A * | 7/1998 | Frezza | A61M 5/2033 604/131 |
| 5,957,897 | A * | 9/1999 | Jeffrey | A61M 5/2033 604/110 |
| 6,203,529 | B1 * | 3/2001 | Gabriel | A61M 5/3202 604/192 |
| 6,210,369 | B1 * | 4/2001 | Wilmot | A61M 5/2033 604/157 |
| 6,743,203 | B1 * | 6/2004 | Pickhard | A61M 5/002 604/110 |
| 2001/0005781 | A1 * | 6/2001 | Bergens | A61M 5/2033 604/208 |
| 2001/0056263 | A1 * | 12/2001 | Alchas | A61M 5/46 604/193 |
| 2002/0183690 | A1 | 12/2002 | Arnisolle | |
| 2004/0039337 | A1 | 2/2004 | Letzing | |
| 2004/0044316 | A1 | 3/2004 | Greenfield | |
| 2004/0054327 | A1 | 3/2004 | Gillespie | |
| 2007/0078394 | A1 * | 4/2007 | Gillespie, III | A61M 5/2033 604/134 |
| 2011/0319834 | A1 | 12/2011 | Modi | |
| 2013/0178823 | A1 | 7/2013 | Buchine et al. | |

FOREIGN PATENT DOCUMENTS

| | | |
|---|---|---|
| GB | 2319184 A | 5/1998 |
| WO | 0211793 A1 | 2/2002 |
| WO | 03039633 A2 | 5/2003 |
| WO | 2007011888 A2 | 1/2007 |
| WO | 2008063439 A2 | 5/2008 |
| WO | 2012/022810 A2 | 2/2012 |
| WO | 2012059449 A1 | 5/2012 |
| WO | 2014080020 A1 | 5/2014 |

* cited by examiner

DRUG DELIVERY DEVICE WITH A HYDRAULIC TRIGGER MECHANISM

CROSS-REFERENCE TO RELATED APPLICATIONS

This application is a 35 U.S.C. § 371 National Stage application of International Application PCT/EP2015/080961 (published as WO 2016/107789), filed Dec. 22, 2015, which claims priority to European Patent Applications 14200378.9, filed Dec. 29, 2014 and 15150309.1, filed Jan. 7, 2015, the contents thereof which are incorporated by reference in their entirety.

The present invention relates in one aspect to a device for administering a liquid medicament by injection. According to a broader aspect, the invention relates to a trigger mechanism for use in a device for the delivery of a liquid medicine.

BACKGROUND OF THE INVENTION

To avoid that the administration of liquid medicine by injection requires the presence of medically trained personnel, numerous drug delivery devices have been developed allowing an untrained user to perform the injection. Ease of use, safety and reliability of such devices are therefore of the utmost importance. Furthermore, end-user acceptance plays a very important role. Such devices may be applicable in numerous contexts. For example, such devices are useful for administration of a liquid drug for the treatment of a chronic disease, such as for the regular injection of an appropriate dose of insulin by a patient himself/herself. Such devices are also useful for emergency use, such as paramedic use, or for applying an antidote against a toxic chemical agent. Typically, these devices are designed upon actuation to automatically perform an appropriate needle insertion to an injection site and subsequently trigger an injection of a dose of the liquid medicine into the tissue at the injection site. However, these known devices typically comprise complex mechanisms for both the injection step and the dosing step and many of these devices are not necessarily easy to use, e.g. because they require a number of distinct steps for appropriately inserting the needle at the site of injection, and subsequently actuating the dosing mechanism. Some devices also allow for automatic triggering of the dosing step for injecting the liquid once the needle is inserted to the injection site. However, in such automatic devices this is achieved at the expense of a complex trigger and dosing mechanism resulting in a bulky device that is also expensive to produce.

Therefore, there is a need for an improved injection device with a simplified mechanical design, which is easy and safe to use. According to one aspect, the object of the present invention is therefore to provide such an improved injection device overcoming at least some of the above-mentioned disadvantages of the prior art, or at least providing an alternative. According to a broader aspect, the object of the present invention is to provide an improved mechanism for use in such injection devices or at least providing an alternative to known mechanisms.

SUMMARY OF THE INVENTION

According to one aspect, the object is achieved by a device for administering a liquid medicament by injection according to claim 1. Further advantageous embodiments are disclosed in the corresponding dependent claims and the description below.

A first aspect of the invention relates to a device for administering a liquid medicament by injection, the device comprising
  a dosing portion with a collapsible reservoir, the reservoir having a first volume (e.g. a maximum volume) in an extended state and a second volume (e.g. a minimum volume) in a collapsed state, wherein prior to injection the reservoir is in the extended state and contains a liquid to be administered, and wherein the reservoir is biased towards the collapsed state, causing a hydrostatic pressure in the liquid;
  an injection needle, wherein a lumen of the needle is in fluid communication with the reservoir; and
  a shield portion with a plug, wherein prior to injection the shield portion is in a deployed position where the plug blocks the lumen of the needle and maintains the hydrostatic pressure in the liquid, and wherein the shield portion is adapted to move in response to an actuation force from the deployed position to a retracted position where the lumen of the needle is open, thereby causing the reservoir to shift to the collapsed state by expelling the liquid through the needle.

The collapsible reservoir is defined by peripheral walls that may move with respect to each other. At least a portion of at least one of the walls defining the reservoir are loaded with a bias force when the reservoir is in the extended state, wherein the bias force biases the reservoir towards the collapsed state where the volume is smaller than the first volume, e.g. a minimum. Prior to injection, the liquid medicine is kept in the reservoir. The bias force applied by at least one of the walls of the reservoir pressurizes the liquid. The reservoir is in fluid communication with the lumen of the injection needle, and the pressure in the liquid is maintained against a counterforce provided by the plug blocking the lumen of the injection needle. The hydraulic leverage of the plug as compared to the bias force exerted by the reservoir walls may be determined by comparison of the cross-sectional area of the lumen of the needle to the area of the reservoir walls according to their contribution to the bias force. Since the lumen of a typical injection needle is significantly smaller than the total area of the reservoir walls that are subject to bias forces, a considerable hydraulic leverage is achieved. This allows for maintaining the liquid medicine under pressure from the biased reservoir by hydraulic means, without the need for any further retaining means for holding the reservoir against the bias force in the extended state.

The collapsible reservoir may be generally rigid, partially flexible or fully flexible. For example, the collapsible reservoir may comprise a cartridge having a cylindrical body which is closed at a neck portion by a penetrable septum and sealed opposite thereto by a slidable piston. In particular, the cartridge may be a 1.5 ml or a 3 ml cartridge as known e.g. from insulin pens used in the diabetes care segment. In that case the injection needle may initially be arranged to extend through the penetrable septum such that one end of the injection needle resides in an interior of the cartridge and the other end resides in the plug. Alternatively, the collapsible reservoir may e.g. comprise a pouch or bag, a bellows-type container, or a rigid base with a flexible sheet attached thereto.

The shield portion holds the plug. Applying an actuation force to the shield causes a movement of the shield from the deployed position to a retracted position, thereby removing the blockage of the lumen of the injection needle. Due to the bias of the reservoir towards the collapsed state, the reservoir collapses upon opening of the fluid passage through the lumen of the needle and the liquid contained in the reservoir is expelled. Moving the shield portion from the deployed position towards the retracted position thus triggers delivery of the liquid medicine without the need for any further trigger mechanism. The difference in volume between the extended state and the collapsed state corresponds to a stroke of the collapsible volume. Considering the incompressibility of liquids underlying the present invention, the stroke determines the dose of the liquid to be delivered.

As mentioned above, the bias of the reservoir towards the collapsed state produces a hydrostatic pressure in the liquid and a counterforce provided by the plug in the lumen maintains the hydrostatic pressure inside the reservoir. Advantageously, the hydraulic leverage of the plug with respect to the bias exerted by the walls of the reservoir via the liquid when the reservoir is in the extended state is at least (1:50), alternatively at least (1:100), alternatively at least (1:500), alternatively at least (1:1000), or even at least (1:5000).

Further according to some embodiments, the plug is arranged at the tip of the needle when the shield is in the deployed position. In the deployed position of the shield portion, the needle tip may be inserted into the plug without penetrating it, thereby blocking for the passage of liquid through the lumen of the needle. Further according to some embodiments, the plug is adapted to be pierced by the needle as the plug moves from the deployed position to the retracted position thereby opening the lumen of the needle. This allows for a simple way of opening the lumen of the needle to trigger the liquid to be expelled from the reservoir. Further according to some embodiments, the shield portion comprises a resting surface arranged at a proximal end of the device. Further according to some embodiments, the shield portion is displaceable in an axial direction with respect to the needle from a deployed position where the plug blocks the lumen of the needle, to a retracted position where the plug is pierced by the needle such that the lumen of the needle is open for fluid passage. In response to an axial actuation force parallel to the direction of the needle, the needle pierces the plug and the plug moves along the needle from the deployed position to the retracted position. In the retracted position the needle has pierced the plug and the lumen of the needle is unblocked, i.e. the lumen of the needle is open for the passage of liquid. This allows for a particularly simple and easy actuation of the device with a single actuation gesture, namely pressing the device in an axial orientation parallel to the needle with a proximal surface of the plug against the skin, thereby piercing the plug with the needle and further pushing the needle into the tissue beneath the skin. Thereby, the lumen of the needle is opened, and the dosing mechanism injects the liquid medicine to the injection site in the tissue according to the penetration depth of the needle. The penetration depth may be controlled by controlling how much the needle in the retracted position of the plug projects beyond the proximal surface as further detailed below.

The shield portion holds the plug and comprises the resting surface wherein the resting surface is adapted for resting against an outer surface of a patient, typically the skin of the patient. The needle is adapted for penetrating tissue of the patient to reach the site of injection. For administration of the liquid medicine by injection to an injection site in a patient, the resting surface of the shield portion arranged at a proximal end of the device is typically brought in contact with the skin of the patient at the injection site. The dosing portion is then pushed towards the shield portion by applying an actuation force in an axial direction to a distal end of the device. The shield portion is thereby pushed from the deployed position to the retracted position, whereby the needle pierces the plug and continues into the tissue. Removal of the plug from the lumen of the needle triggers the device to expel the liquid medicine through the needle as described above, and the liquid medicine is delivered to the injection site in the patient. The depth of the delivery is determined by the length of the needle projecting from the resting surface when the shield portion is in the retracted position.

Thereby, a reliable drug delivery device for the administration of a liquid medicine, such as e.g. insulin, glp-1, or a combination thereof, by injection is achieved, which has a simplified mechanics, is easy to produce and is particularly easy and safe to use. Further advantages include a compact design with a small form factor. The needle insertion and trigger mechanism are integrally coupled and are driven by the same actuation movement.

The small diameter of the needle and the sharp tip is furthermore advantageous for the easy removal of the plug by merely piercing the plug with the needle. Furthermore, due to the hydraulic leverage the plug does not have to be so thick and solid. A reduction of the force required for piercing the plug also reduces the actuation force when actuating the device in a single gesture, such as pressing the device with its resting surface to the surface of the skin at the injection site with a force equal to or exceeding an actuation force of the device. An excessive actuation force may be difficult to control and might be inhibitive for the "single movement/gesture" actuation, in particular when performed by untrained users.

Further according to some embodiments of the device, the shield portion is biased towards the deployed position by means of a shield bias element. The shield bias element may be of any suitable kind, such as an elastic element. Thereby it is ensured that the shield in absence of an actuation force is placed in the deployed position. Prior to use, this helps to protect the needle and keep the lumen of the needle plugged to avoid inadvertent ejection of the liquid from the reservoir. Furthermore, the bias may be adapted to adjust the force required for actuation of the device to a predetermined value. Most preferably, the shield bias element is configured such that the shield returns to the deployed position, when removing the device from the injection site after use. Thereby improved safety of the device after use, and in particular after disposal, is achieved.

Further according to some embodiments of the device, the shield bias is an elastic element, preferably a compression spring. The compression spring may be of any suitable kind, e.g. a helicoidally wound compression spring. A shield bias compression spring may advantageously be arranged between the shield portion and the dosing portion. For example when using a syringe as the collapsible reservoir, one end of the compression spring may abut the barrel, while the opposite end may abut an inner face of the shield portion. Analogue to the above embodiment, the spring constant of the elastic element may be adapted to provide a predetermined value for the actuation force. Further preferably, the spring constant is configured to return the shield to the deployed position after use.

Further according to some embodiments of the device, the shield fully encases the needle. Thereby, an improved protection of the needle, and an improved protection of a user against injuries is achieved. Furthermore, the needle is thereby concealed from the regard of the user, which is a considerable advantage for users suffering from needle-phobia.

Further according to some embodiments of the device, the needle is encapsulated by a sterile encapsulation. While the shield portion may protect the needle, it may not be sufficient to maintain sterile conditions for the injection needle. This is advantageously achieved by protecting the injection needle immediately upon loading the reservoir with the liquid medicament under pharmaceutically clean production conditions. Consequently, the mechanical parts of e.g. the shield portion encasing the needle need not be produced and assembled under the same stringent clean room conditions of pharmaceutical production. Thereby a reduction in production cost is achieved.

Further according to some embodiments of the device, the displacement of the shield and syringe portions with respect to each other is guided by guide means, such as guide rails and cooperating lugs. Thereby it is achieved that the shield portion performs a well-defined displacement motion with respect to the dosing portion, thus ensuring a well-controlled actuation and injection procedure, which is less sensitive to the fine motor skills of the untrained user.

Further according to some embodiments of the device, the guide means comprise distal and/or proximal end stops for limiting the displacement of the shield portion with respect to the dosing portion. A first end stop defines a deployed position of the shield portion, thereby ensuring that the plug does not come off accidentally. A second end stop defines a retracted position of the shield portion to control injection depth. Injection depth is determined by the distance, by which the needle tip projects from the resting surface at the proximal end of the shield when the shield portion is in the retracted position.

Further according to some embodiments of the device, the dosing portion comprises a housing, wherein the housing encases the collapsible reservoir. The housing protects the collapsible reservoir, and may house mechanical elements for providing a bias to the reservoir towards the collapsed state as well as elements cooperating with the shield portion for governing the movement of the shield portion with respect to the dosing portion. According to some embodiments the housing may be produced separate from the parts requiring a particularly clean production environment. This facilitates production and loading of medicaments in the reservoir under sterile conditions, or at least in a particularly clean production environment, while producing and assembling outer housing/mechanical parts, such as parts for user friendly actuation, under less stringent production conditions.

Further according to some embodiments of the device, the dosing portion comprises a syringe with a barrel and a cooperating plunger, wherein the barrel and the plunger in combination define the collapsible reservoir, wherein the plunger is displaceable inside the barrel from a first position corresponding to the first volume of the reservoir to a second position corresponding to the second volume of the reservoir, wherein the plunger is biased towards the second position by means of a plunger bias element. Using a syringe as the collapsible reservoir is a particularly advantageous embodiment. For example, it allows for a simple actuation by a single gesture, such as an axial movement for the insertion of the injection needle at the injection site and at the same time providing a simple dosing mechanism with a well-defined stroke for the precise dosing of the liquid to be administered. Most preferably, the plunger stroke is a movement parallel to an axial direction defined by the injection needle.

Further according to some embodiments of the device, the barrel is integrally formed with the housing. Thereby the number of assembly steps may be reduced, thus reducing production cost.

Further according to some embodiments of the device, the plunger bias element is an elastic element, preferably a compression spring. The compression spring may be of any suitable kind, e.g. a helicoidally wound compression spring. A plunger bias compression spring may advantageously be arranged between a housing and a moveable wall part of the reservoir. For example when using a syringe as the collapsible reservoir, one end of the compression spring may abut a stem on the rear side of the plunger, while the opposite end may abut an inner face of a housing part.

Further according to some embodiments of the device, a ratio (A1:A2) of the cross-sectional area A1 of the lumen of the needle over the cross-sectional area of the plunger A2 is at least (1:50), alternatively at least (1:100), alternatively at least (1:500), alternatively at least (1:1000), or even at least (1:5000). Since the lumen of a typical injection needle is significantly smaller than the area of the biased plunger of the syringe, a considerable hydraulic leverage is easily achieved.

According to a broader aspect of the invention a mechanism for delivering a liquid through a needle comprises a collapsible reservoir for holding the liquid to be delivered, the reservoir having a maximum volume in an extended state and a minimum volume in a collapsed state, wherein walls defining the reservoir are biased towards the collapsed state. The mechanism further comprises an injection needle, wherein a lumen of the needle is in fluid communication with the reservoir, and a plug arranged in a deployed position so as to block the lumen of the needle, wherein the plug is adapted to be moved in response to an actuation force from the deployed position to a retracted position where the lumen is unblocked. Preferably, the plug is arranged in a deployed position at the tip of the injection needle so as to block the lumen of the needle, wherein the plug is adapted to be pierced by the needle when an axial actuation force is applied pushing the plug and the needle towards each other. The mechanism is operated as discussed with respect to the above-disclosed drug delivery device. The mechanism is particularly useful in a device for the dosed injection of a liquid at an injection site, such as hypodermal injection of a liquid medicine in a patient. Preferably, the mechanism is implemented using a syringe with a barrel and a cooperating plunger as the collapsible reservoir, wherein the volume of the reservoir depends on the position of the plunger with respect to the barrel of the syringe as described above, wherein a first position of the plunger corresponds to the extended state of the reservoir and is associated with the maximum volume, and wherein a second position of the plunger corresponds to the collapsed state of the reservoir is associated with the minimum volume. A bias towards the collapsed state may be provided by means of a plunger bias element as also described above. Further advantageous embodiments of the mechanism using a syringe as the collapsible reservoir may be derived accordingly from the above-mentioned embodiments of the device for administering a liquid medicine.

In a further aspect of the invention an injection device is provided comprising a pressurised reservoir holding a volume of substance, an injection needle structure comprising an inlet end portion in permanent fluid communication with the pressurised reservoir and an outlet end portion fluidly connected with the inlet end portion and adapted to penetrate a skin barrier, and an elastomeric plug for initial sealing of the outlet end portion, the elastomeric plug being movable along the injection needle structure between a first position in which the outlet end portion resides within the elastomeric plug and a second position in which the injection needle transpierces the elastomeric plug and the outlet end portion is exposed. The outlet end portion and the inlet end portion are fluidly connected via a lumen of the injection needle structure. The lumen is blocked when the elastomeric plug is in the first position, and, as previously described, the substance is thereby maintained under pressure in the reservoir. When the elastomeric plug is moved to the second position the lumen is opened to the surroundings, e.g. to the skin insertion site, and substance is automatically expelled through the outlet end portion.

The injection needle structure may extend along a longitudinal axis and may be fixed axially with respect to the pressurised reservoir to thereby provide for an exposure of the outlet end portion, and thereby initiation of an automatic expelling of substance, by simple linear motion of the elastomeric plug relative to the injection needle structure.

The injection device may further comprise a plug holding structure for stabilising the movements of the elastomeric plug along the injection needle structure. The plug holding structure may be configured to move linearly with respect to the reservoir between an extended position in which the elastomeric plug is in the first position and a retracted position in which the elastomeric plug is in the second position. The movements of the plug holding structure may be guided by a housing or sheath accommodating at least a portion of the reservoir.

In some embodiments of the invention the plug holding structure comprises a cylindrical portion extending along the axis of the injection needle structure, thereby forming a needle shield for the injection needle structure. In other embodiments of the invention the plug holding structure comprises a plurality of axially extending arms, in lieu of a circumferentially closed structure, such that at least a portion of the injection needle structure between the inlet end portion and the outlet end portion is both visible and accessible to a user.

The plug holding structure may be biased towards the extended position such that a plug bias force must be overcome to move the elastomeric plug to the second position. The plug bias force may be dimensioned to be overcome by a light or moderate depression of the elastomeric plug towards a skin site, and to return the elastomeric plug to the first position upon removal of the elastomeric plug from the skin. Thereby, the risk of accidental needle stick injuries is reduced.

In the present specification, reference to a certain aspect or a certain embodiment (e.g. "an aspect", "a first aspect", "one embodiment", "an exemplary embodiment", or the like) signifies that a particular feature, structure, or characteristic described in connection with the respective aspect or embodiment is included in, or inherent of, at least that one aspect or embodiment of the invention, but not necessarily in/of all aspects or embodiments of the invention. It is emphasized, however, that any combination of the various features, structures and/or characteristics described in relation to the invention is encompassed by the invention unless expressly stated herein or clearly contradicted by context.

The use of any and all examples, or exemplary language (e.g., such as, etc.), in the text is intended to merely illuminate the invention and does not pose a limitation on the scope of the same, unless otherwise claimed. Further, no language or wording in the specification should be construed as indicating any non-claimed element as essential to the practice of the invention.

BRIEF DESCRIPTION OF THE DRAWINGS

Preferred embodiments of the invention will be described in more detail in connection with the appended drawings, which show in FIG. 1 a cross-sectional view of a device according to one embodiment of the invention, and in FIG. 2 cross-sectional views of the device of FIG. 1: (a) prior to the injection procedure; (b) during the injection procedure; and (c) after the injection procedure.

DETAILED DESCRIPTION OF PREFERRED EMBODIMENTS

Figure 1:
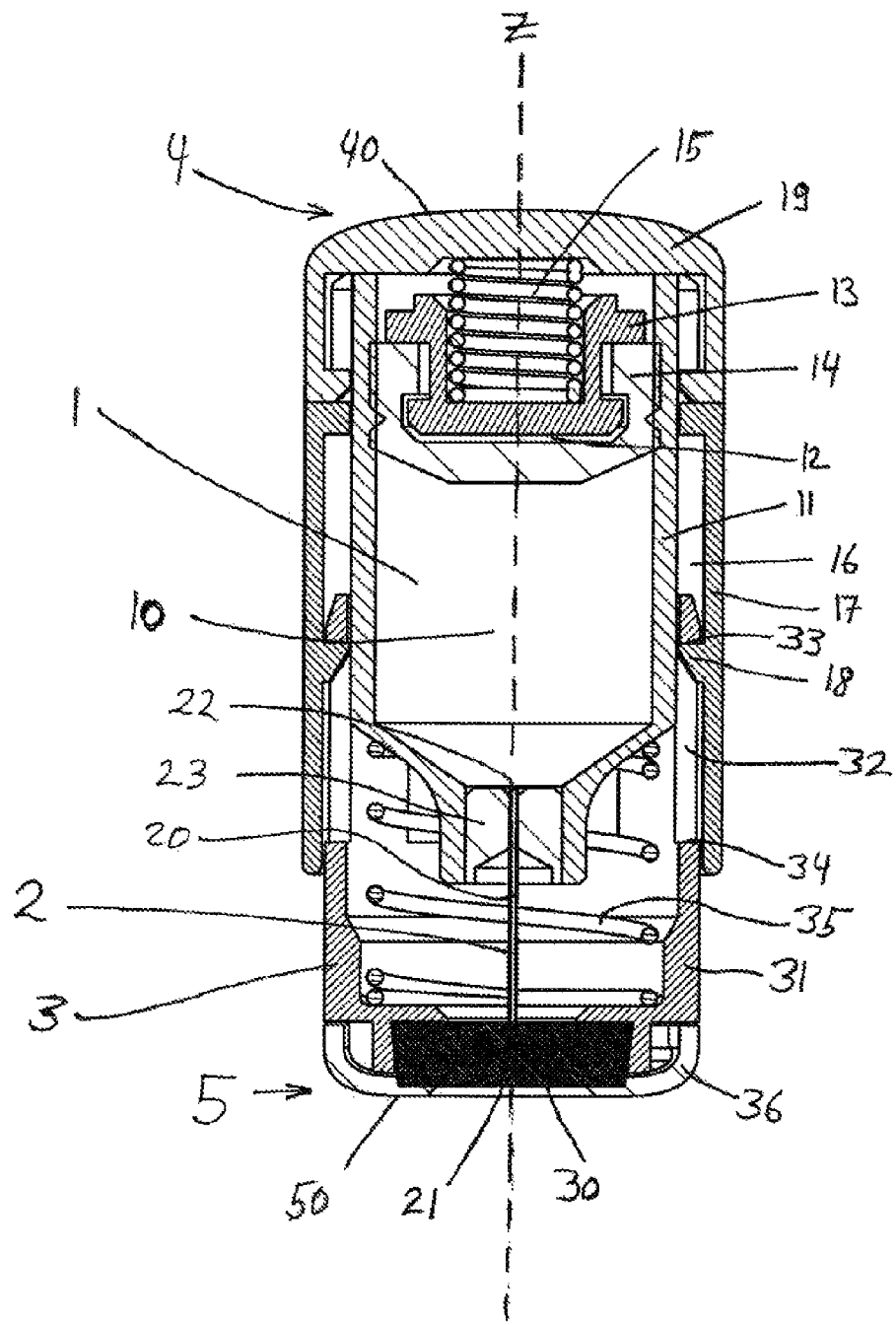
Figure 2A:
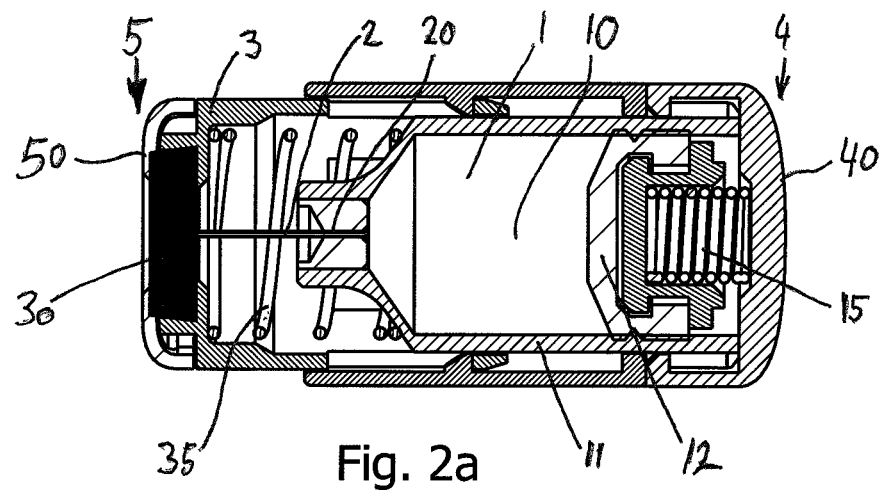
Figure 2B:
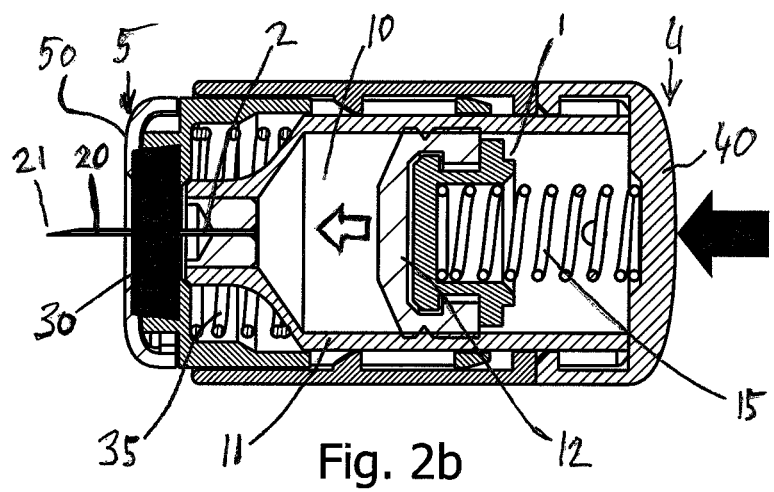
Figure 2C:
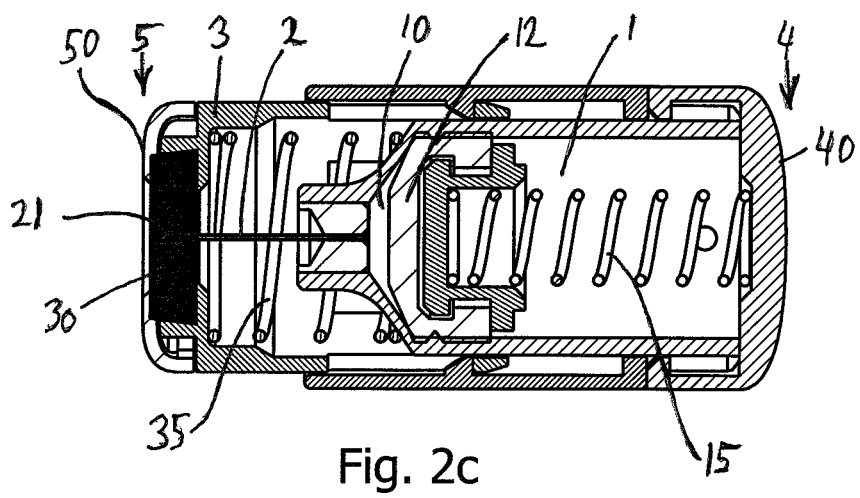

FIG. 1 and FIG. 2 show side cross-sectional views of a device for administering a liquid medicament by injection according to one embodiment. FIG. 1 shows the device prior to use, FIG. 2a shows the device prior to use, FIG. 2b shows the device during injection, and FIG. 2c shows the device after use.

The device comprises a dosing portion 1 with a collapsible reservoir 10, the reservoir 10 having a maximum volume in an extended state and a minimum volume in a collapsed state, wherein prior to injection the reservoir 10 is in the extended state and contains a liquid to be administered (not shown), and wherein the reservoir is biased towards the collapsed state. The device further comprises an injection needle 2, wherein a lumen 20 of the needle 2 is in fluid communication with the reservoir 10. The device further comprises a shield portion 3 with a plug 30, wherein prior to injection the shield portion 3 is in a deployed position where the plug 30 blocks the lumen 20 of the needle 2, and wherein the shield portion 3 is adapted to move in response to an actuation force from the deployed position to a retracted position where the lumen 20 of the needle 2 is open, thereby causing the reservoir 10 to shift to the collapsed state to expel the liquid through the needle 2.

Referring to FIG. 1, the collapsible reservoir 10 of the dosing portion 1 is formed as a syringe with a barrel 11 and a plunger 12. The plunger 12 has a stem 13 at a rear side facing away from the volume of the reservoir 10 and a seal 14 capping the plunger 12 at a front side facing towards the volume of the reservoir 10 and sealing the plunger 12 against the inner walls of the barrel 11. The syringe is encased by a housing 16 with a peripheral sheath portion 17 and an end cap 19 forming a distal end 4 of the device. The volume of the reservoir 10 depends on the position of the plunger 12 with respect to the barrel 11. In the extended state of the reservoir 10, the plunger is in a first position at a distal end of the barrel 11 such that the volume of the reservoir 10 is a maximum. In the collapsed state of the reservoir 10, the plunger is in a second position at a proximal end of the barrel, such that the volume of the reservoir 10 is a minimum. The reservoir 10 is biased to the collapsed state by means of a plunger bias element 15 applying a bias force to the plunger 12 in a direction towards the second position. The plunger bias element 15 is a compression spring abutting at one end the stem 13 on the rear side of the plunger 12 and at an opposite end the inside of the end cap 19. In the extended state of the reservoir 10 shown in FIG. 1 and FIG.

2a, the compression spring is compressed and in the collapsed state of the reservoir shown in FIG. 2c, the compression spring is expanded.

The injection needle 2 is oriented in the axial direction and is arranged at a proximal end of the barrel 11, opposite to the plunger 12. A distal end of the needle 2 is fixed to the barrel 11 with a needle mount 23 sealing the reservoir 10 at its proximal end. The lumen 20 of the needle 2 is in fluid communication with the reservoir 10 through an inlet opening 22 at the distal end of the needle 2. An outlet opening at the tip 21 at the proximal end of the needle 2 is inserted in the plug 30 without penetrating it, thereby blocking the lumen 20 of the needle 2.

The device further comprises a shield portion 3 holding the plug 30 in place at the tip 21 of the needle 2, when the shield portion 3 is in a deployed position. The shield portion 3 comprises a resting surface 50 arranged at a proximal end 5 of the device. The shield portion 3 is displaceable in an axial direction with respect to the needle 2 from the deployed position where the plug 30 blocks the lumen 20 of the needle 2, to a retracted position where the plug 30 is pierced by the needle 2 such that the lumen 20 of the needle 2 is open for fluid passage.

The axial movement of the shield portion 3 with respect to the dosing portion 1 is guided by guiding means 18, 32 with end stops 33, 34 determining the length of the travel. Here, the guiding means include guide rails 32 in the form of axially extending slots arranged on the side of the shield portion 3 and cooperating lugs 18 on the peripheral sheath 17 of the dosing portion housing. The lugs 18 interact with the distal end stop 33 on the guide rail 32 to define the deployed position of the shield portion 3, and with the proximal end stop 34 on the guide rail 32 to define the retracted position of the shield portion 3.

The shield portion 3 is biased towards the deployed position by means of a shield bias element 35, here in the form of a compression spring acting in the axial direction between the barrel 11 and the shield portion 3. The shield portion 3 fully encases the needle 2 when the shield is in the deployed position. The needle 2 projects from the resting surface 50 when the shield portion 3 is in the retracted position, wherein an axial distance of the needle tip 21 from the resting surface 50 corresponds to an injection depth.

In its extended state, the reservoir 10 is loaded with a liquid medicine for administration by injection, wherein the bias of the plunger 12 applies a pressure to the liquid. Since the plug 30 blocks for the passage of the fluid through the lumen 20 of the needle, it maintains the hydrostatic pressure inside the reservoir 10. The plug 30 communicates hydraulically with the plunger 12 via the liquid in the reservoir 10. The force required for keeping the plug 30 in place corresponds to the hydraulic force exerted on the plug 30 by the liquid. The hydraulic counter force exerted on the liquid by the plug 30 for maintaining the hydrostatic pressure in the reservoir 10 equals the bias force exerted on the liquid by the plunger 12 scaled down by the ratio of the cross-sectional area of the lumen 20 over the cross-sectional area of the plunger 12: F1(plug)=F2(plunger)×(A1(plug)/A2(plunger)), wherein the areas are taken in a cross-sectional plane perpendicular to the axial direction. The ratio (A1:A2) of the cross-sectional area A1 of the lumen of the needle over the cross-sectional area of the plunger A2 corresponds here to the hydraulic leverage of the plug with respect to the bias exerted by the plunger via the liquid in the reservoir. Since the lumen of a typical injection needle is significantly smaller than the cross-section of the barrel, a considerable hydraulic leverage is achieved. This allows for maintaining the liquid medicine under pressure from the biased plunger 12 by hydraulic means without the need for any further retaining means for holding the plunger 12 against the bias force in the first position. Advantageously, the ratio of the cross-sectional areas (A1:A2) and thus the hydraulic leverage is at least (1:50), alternatively at least (1:100), alternatively at least (1:500), alternatively at least (1:1000), or even at least (1:5000).

When the shield portion 3 is displaced from the deployed position towards the retracted position, the plug 30 is pierced by the needle 2, thereby opening the lumen 20 for fluid passage there through. The hydraulic counter force provided by the plug 30 to retain the biased plunger 12 in its first position is thus removed, and the plunger 12 moves from the first position to the second position. The displacement of the plunger 12 expels the liquid from the reservoir 10 through the needle 2 to the outside. In this way, piercing the needle 2 through the plug 30 by pushing the shield portion 3 towards the retracted position triggers delivery of the liquid medicine without the need for any further trigger mechanism.

A sequence of operation of the device is described in more detail by referring to FIG. 2 in the following. FIG. 2a shows the device prior to use loaded with a liquid medicine for administration to a patient by injection. Prior to use, the reservoir 10 is in the extended state where the plunger 12 is in the first position at the distal end of the barrel 11 and where the plunger bias element 15 is fully compressed. The shield portion 3 is held in the deployed position by the compression spring 35, which is expanded when the shield 3 is deployed. The shield portion 3 holds the plug 12 and comprises the resting surface 50 at the proximal end 5 of the device. The resting surface 50 is adapted for resting against an outer surface of a patient, typically the skin of the patient. The plug 30 blocks the lumen 20 of the needle 2, thereby maintaining the liquid under pressure as described above. For administration of the liquid medicine by injection to an injection site in a patient (not shown), the resting surface 50 of the shield portion 3 is typically brought in contact with the skin of the patient at the injection site. The dosing portion 1 is then pushed towards the shield portion 3 by applying an actuation force in an axial direction to an actuation surface 40 at a distal end 4 of the device as indicated by the black block arrow in FIG. 2b. The shield portion 3 is thereby pushed from the deployed position to the retracted position as best seen in FIG. 2b. The needle 2 is adapted for piercing the plug 30 and penetrating tissue of the patient to reach the site of injection. Under the continued action of the actuation force, the needle 2 therefore pierces the plug 30 and continues into the tissue. Removal of the plug 30 from the lumen 20 of the needle 2 allows the plug 12 under the action of the plunger bias element 15 to move towards the second position as indicated by the hollow block arrow in FIG. 2b. Removal of the plug 30 thus triggers the device to expel the liquid medicine through the needle as described above, and the liquid medicine is delivered to the injection site in the patient, wherein the depth of the delivery is determined by the length of the needle 2 projecting from the resting surface 50 when the shield portion 3 is in the retracted position. In the retracted position of the shield 3, the shield bias element 35 is compressed.

Thereby a reliable drug delivery device for the administration of a liquid medicine by injection is achieved, which has a simplified mechanics, is easy to produce and is particularly easy and safe to use. Further advantages include a compact design with a small form factor. The needle insertion and trigger mechanism are integrally coupled and are driven by the same actuation movement. The small diameter of the needle and the sharp tip is furthermore advantageous for the easy removal of the plug by merely piercing the plug with the needle. Furthermore, due to the hydraulic leverage the plug does not have to be so thick and solid. A reduction of the force required for piercing the plug also reduces the actuation force when actuating the device in a single gesture, such as pressing the device with its resting surface to the surface of the skin at the injection site with a force equal to or exceeding an actuation force of the device. An excessive actuation force might be inhibitive for the "single movement/gesture" actuation, in particular when performed by untrained users.

FIG. 2c shows the device after use, where the actuation-force has been removed. The shield 3 returns to the deployed position under the action of the shield bias element 35 and guided by the guiding means 18, 32, 33, 34 as described above with respect to FIG. 1. The deployment of the shield portion 3 helps removing the needle from the injection site. After removal of the device from the injection site, the deployed shield 3 avoids any unintended contact with the needle, thereby preventing injuries and avoiding the spreading of any infections. Note that after the liquid has been expelled, there is no counterforce any longer that would act against the bias of the reservoir 10 and the reservoir 10 therefore remains in the collapsed state. In the embodiment shown here, this means that the plunger 12 remains in the second position where the volume of the reservoir 10 is a minimum and the plunger bias element 15 is expanded.

REFERENCE NUMBERS 1 dosing portion
2 needle
3 shield portion
4 distal end
5 proximal end
10 reservoir
11 barrel
12 plunger
13 stem
14 seal
15 plunger bias element
16 housing
17 sheath
18 lug
19 cap
20 lumen
21 tip
22 inlet
23 needle mount
30 plug
31 jacket
32 guide rail
33 distal end stop (deployed shield)
34 proximal end stop (retracted shield)
35 shield bias element
36 cover
50 resting surface
Z axial direction

The invention claimed is:

1. A device for administering a liquid by injection, the device comprising:
    a dosing portion with a collapsible reservoir, the collapsible reservoir having a maximum volume in an extended state and a minimum volume in a collapsed state, wherein prior to injection: the collapsible reservoir is in the extended state, contains a liquid to be administered, and is biased towards the collapsed state, wherein the dosing portion comprises a syringe with a barrel and a cooperating plunger, wherein the barrel and the plunger in combination define the collapsible reservoir, wherein the plunger is displaceable inside the barrel from a first position corresponding to the maximum volume of the collapsible reservoir, to a second position corresponding to the minimum volume of the collapsible reservoir, wherein the plunger is biased towards the second position by a compression spring;
    an injection needle, wherein a lumen of the injection needle is in fluid communication with the collapsible reservoir;
    a shield portion comprising a plug, wherein prior to injection, the shield portion is in a deployed position where the plug shields and blocks the lumen of the injection needle thereby preventing the liquid from moving out of the collapsible reservoir, whereby the liquid is maintained under pressure in the collapsible reservoir, and wherein the shield portion is adapted to move in response to an actuation force applied to the shield portion from the deployed position to a retracted position where the lumen of the injection needle is open allowing the liquid to move out of the collapsible reservoir, thereby causing the reservoir to shift to the collapsed state to expel the liquid through the injection needle; and
    wherein actuation of the device is performed by pressing a needle end of the device against a patient's skin at an axial orientation parallel to the injection needle with sufficient force to pierce the plug with the injection needle, whereby the plug acts as a hydraulic trigger mechanism.

2. The device according to claim 1, wherein the plug is arranged at a tip of the injection needle when the shield portion is in the deployed position.

3. The device according to claim 2, wherein the plug is adapted to be pierced by the injection needle as the shield portion moves from the deployed position to the retracted position thereby opening the lumen of the injection needle.

4. The device according to claim 1, wherein the shield portion comprises a resting surface arranged at a proximal end of the device.

5. The device according to claim 4, wherein the shield portion is displaceable in an axial direction with respect to the injection needle from the deployed position to the retracted position, wherein the plug is pierced by the injection needle in the retracted position.

6. The device according to claim 1, wherein the shield portion is biased towards the deployed position by structure of a shield bias element.

7. The device according to claim 6, wherein the shield bias element is a compression spring.

8. The device according to claim 1, wherein the shield portion fully encases the injection needle when in the deployed position.

9. The device according to claim 1, wherein displacement of the shield portion and the dosing portion with respect to each other is guided by a guide structure comprising guide rails and cooperating lugs.

10. The device according to claim 9, wherein the guide structure comprises distal and proximal end stops for limiting the displacement of the shield portion with respect to the dosing portion.

11. The device according to claim 1, wherein the dosing portion comprises a housing, wherein the housing encases the collapsible reservoir.

12. The device according to claim 11, wherein the barrel is integrally formed with the housing.

13. The device according to claim 1, wherein a ratio of a cross-sectional area of the lumen of the injection needle to a cross-sectional area of the plunger is at least 1:50.

14. The device according to claim 1, wherein a ratio of a cross-sectional area of the lumen of the injection needle to a cross-sectional area of the plunger is at least 1:100.

15. The device according to claim 1, wherein a ratio of a cross-sectional area of the lumen of the injection needle to a cross-sectional area of the plunger is at least 1:500.

16. The device according to claim 1, wherein a ratio of a cross-sectional area of the lumen of the injection needle to a cross-sectional area of the plunger is at least 1:1000.

17. The device according to claim 1, wherein a ratio of a cross-sectional area of the lumen of the injection needle to a cross-sectional area of the plunger is at least 1:5000.

* * * * *